(12) United States Patent
Sethi et al.

(10) Patent No.: US 12,589,019 B2
(45) Date of Patent: Mar. 31, 2026

(54) MODIFIED JAW THRUST APPLIANCE

(71) Applicants: Manu Sethi, Canfield, OH (US);
Sangeetha Sethi, Canfield, OH (US)

(72) Inventors: Manu Sethi, Canfield, OH (US);
Sangeetha Sethi, Canfield, OH (US)

( * ) Notice: Subject to any disclaimer, the term of this patent is extended or adjusted under 35 U.S.C. 154(b) by 335 days.

(21) Appl. No.: 18/451,180

(22) Filed: Aug. 17, 2023

(65) Prior Publication Data

US 2025/0057715 A1     Feb. 20, 2025

(51) Int. Cl.
*A61F 5/058*       (2006.01)
*A61F 5/37*        (2006.01)
*A61F 5/56*        (2006.01)

(52) U.S. Cl.
CPC ............ *A61F 5/05891* (2013.01); *A61F 5/37* (2013.01); *A61F 5/3707* (2013.01); *A61F 5/56* (2013.01)

(58) Field of Classification Search
CPC ...... A61F 5/05891; A61F 5/37; A61F 5/3707; A61F 5/055; A61F 5/05883; A61F 5/56; A61F 5/566; A61F 2005/563; A61F 11/145; A61G 13/121; A61G 13/1205; A61G 13/129; A61G 7/072; A61B 17/6433; A61B 90/14; A61B 90/16; A61C 7/06
USPC ........................................................ 128/845
See application file for complete search history.

(56) References Cited

U.S. PATENT DOCUMENTS 532,567   A  *  1/1895  Larwood, Jr. ............ A42B 3/08
                                                    2/421
1,865,827 A  *  7/1932  Bryant ................ A61F 5/05891
                                                    602/17

4,597,738   A      7/1986  Sander et al.
4,782,824   A     11/1988  Davies
5,524,639   A      6/1996  Lanier et al.
5,682,632   A     11/1997  Cotroneo
7,121,824   B2    10/2006  Keles et al.
7,951,102   B2     5/2011  Gefen et al.
8,191,553   B2     6/2012  Haworth et al.
9,730,731   B2 *   8/2017  Langenfeld ........ A61B 17/6433
2008/0173313 A1 *  7/2008  Brady .................. A61B 17/663
                                                    128/848

(Continued)

FOREIGN PATENT DOCUMENTS

CN         115281991    * 11/2022  ............. A61G 13/12
WO   WO 2014102340     *  7/2014  ............. A61F 5/055

OTHER PUBLICATIONS

CN115281991A machine translation (Year: 2022).*

*Primary Examiner* — Adam Baker
(74) *Attorney, Agent, or Firm* — Boudwin Intellectual Property Law, LLC; Daniel Boudwin

(57)                ABSTRACT

A jaw thrust appliance is disclosed. The jaw thrust appliance includes an adjustable slidable bottom movably attached to the bottom portion of the inverted U-shaped base, and an ergonomic thumb piece disposed directly underneath the adjustable slidable bottom, the adjustable slidable bottom and the ergonomic thumb piece are attached together and move as a single unit when pushed horizontally. The inverted U-shaped base includes a flat elongated front facing, a padded back facing, a plurality of raised inverted U-shaped belt loops, and an indicia. The flat elongated front facing is adapted to be curved inward to accommodate the shape of a user's face. The jaw thrust appliance also includes an ergonomic thumb piece disposed directly underneath the adjustable slidable bottom.

19 Claims, 5 Drawing Sheets

(56) References Cited

U.S. PATENT DOCUMENTS

| | | |
|---|---|---|
| 2011/0308528 A1 | 12/2011 | Ciardullo |
| 2012/0186591 A1* | 7/2012 | Sethi ......................... A61F 5/56 |
| | | 128/859 |
| 2020/0038224 A1* | 2/2020 | Dellanno ............... A61F 5/055 |

* cited by examiner

MODIFIED JAW THRUST APPLIANCE

BACKGROUND OF THE INVENTION

The present invention relates to a jaw thrust appliance. More specifically, the present device relates to a modified jaw thrust appliance.

A jaw thrust maneuver is a medical procedure that is used to treat sleeping disorders, treat complications from medical procedures and anesthesia, treat complications from urgent and emergency care, and treat complications from snoring and the like.

The jaw thrust maneuver is performed with a jaw thrust appliance that is often times awkward and does not provide the comfort that is needed to perform the desired medical procedure.

What is needed is a modified jaw thrust appliance that provides the comfort and eliminates the awkwardness associated with a jaw thrust maneuver.

SUMMARY OF THE INVENTION

In view of the foregoing disadvantages inherent in the known types of jaw thrust appliance now present in the prior art, the present invention provides a jaw thrust appliance wherein the same can be utilized for providing convenience for the user when a jaw thrust appliance is in use.

The present system comprises a jaw thrust appliance that includes an inverted U-shaped base having a bottom portion, an adjustable slidable bottom movably attached to the bottom portion of the inverted U-shaped base, and an ergonomic thumb piece disposed directly underneath the adjustable slidable bottom, the adjustable slidable bottom and the ergonomic thumb piece are attached together and move as a single unit when pushed horizontally.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
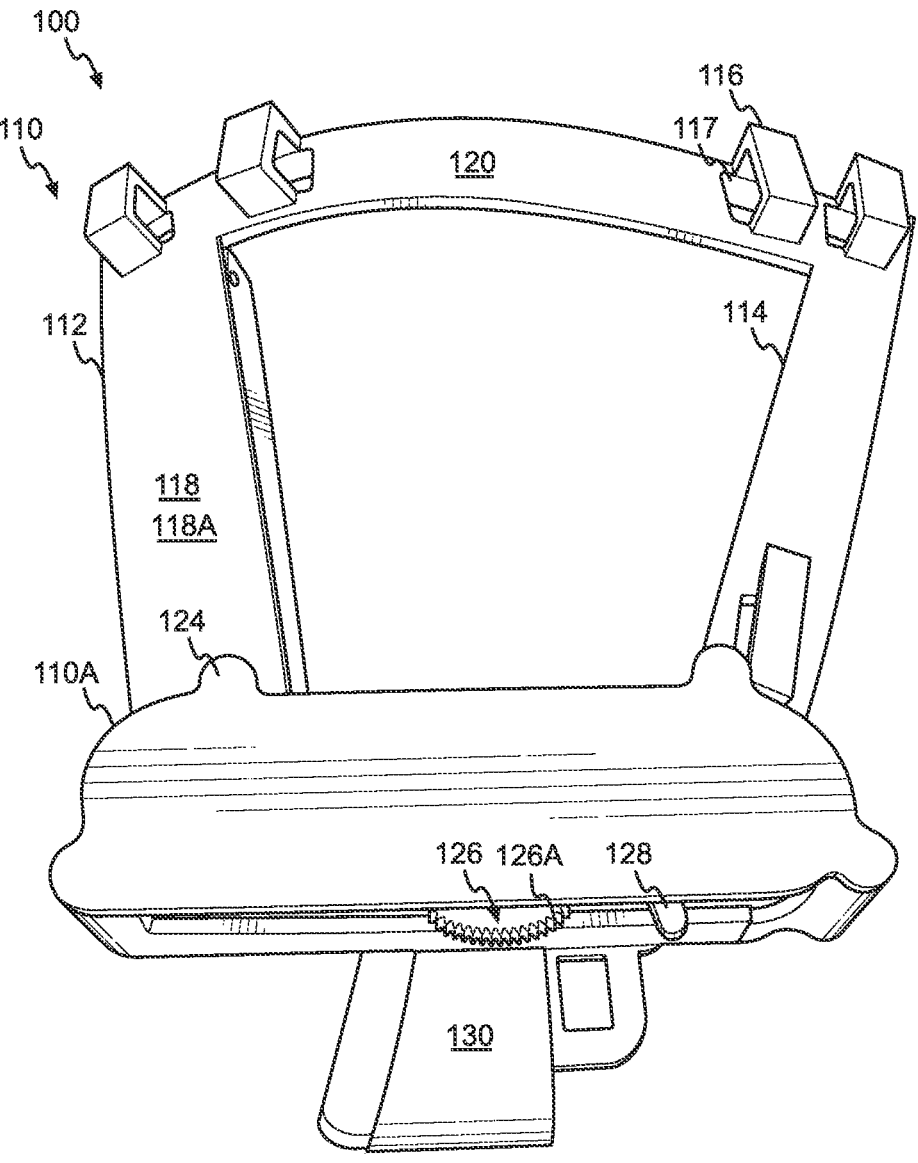
FIG. 1 shows a front perspective view of a jaw thrust appliance, in accordance with one embodiment of the present invention.

Reference is made herein to the attached drawings. Like reference numerals are used throughout the drawings to depict like or similar elements of the self-rocking baby crib.

The figures are intended for representative purposes only and should not be considered to be limiting in any respect.

FIG. 1 shows a front perspective view of a jaw thrust appliance 100, in accordance with one embodiment of the present invention.

The jaw thrust appliance 100 may include an inverted U-shaped base 110, an adjustable slidable bottom 120, and an ergonomic thumb piece 130.

The inverted U-shaped base 110 may have a bottom portion 110A or the like. The inverted U-shaped base 110 may have a flat elongated front facing 112, a padded back facing 114, a plurality of raised inverted U-shaped belt loops 116, and an indicia 118.

The flat elongated front facing 112 may be adapted to be curved inward to accommodate the shape of a user's face. The flat elongated front facing 112 may be made of durable material selected from the group consisting of plastic, metal, ceramic, or any combination of each. The padded back facing 114 may be made of foam rubber or the like to provide comfort to a user while the jaw thrust appliance 100 is being worn. The padded back facing 114 may cushion a user's face but also is breathable for additional comfort. The raised inverted U-shaped belt loops 116 may accommodate a belt (See FIG. 4, 140) or the like that is adapted to secure the jaw thrust appliance 100 to a user's face. The raised inverted U-shaped belt loops 116 may include a rectangular aperture 117 disposed underneath each of the raised inverted U-shaped belt loops 116. The indicia 118 may be a functional indicia 118A such as "Left Front" to insure that a user places the inverted U-shaped base 110 properly on their face. The indicia 118 may be stamped onto the left front portion of the inverted U-shaped base 110 to insure it is not removed or rubbed off or the like.

The adjustable slidable bottom 120 may have an elongated horizontal casing 122, a plurality of raised rounded protrusions 124, a contact wheel 126, and a lever 128. The adjustable slidable bottom 120 may be made of durable material selected from the group consisting of plastic, metal, ceramic, or any combination of each. The adjustable slidable bottom 120 may be described in greater detail in FIGS. 2 and 3 and its description.

The ergonomic thumb piece 130 may be disposed directly underneath the adjustable slidable bottom 120. The ergonomic thumb piece 130 may be made of durable material selected from the group consisting of plastic, metal, ceramic, or any combination of each. The ergonomic thumb piece 130 may be described in greater detail in FIGS. 2 and 3 and its description.

Figure 2:
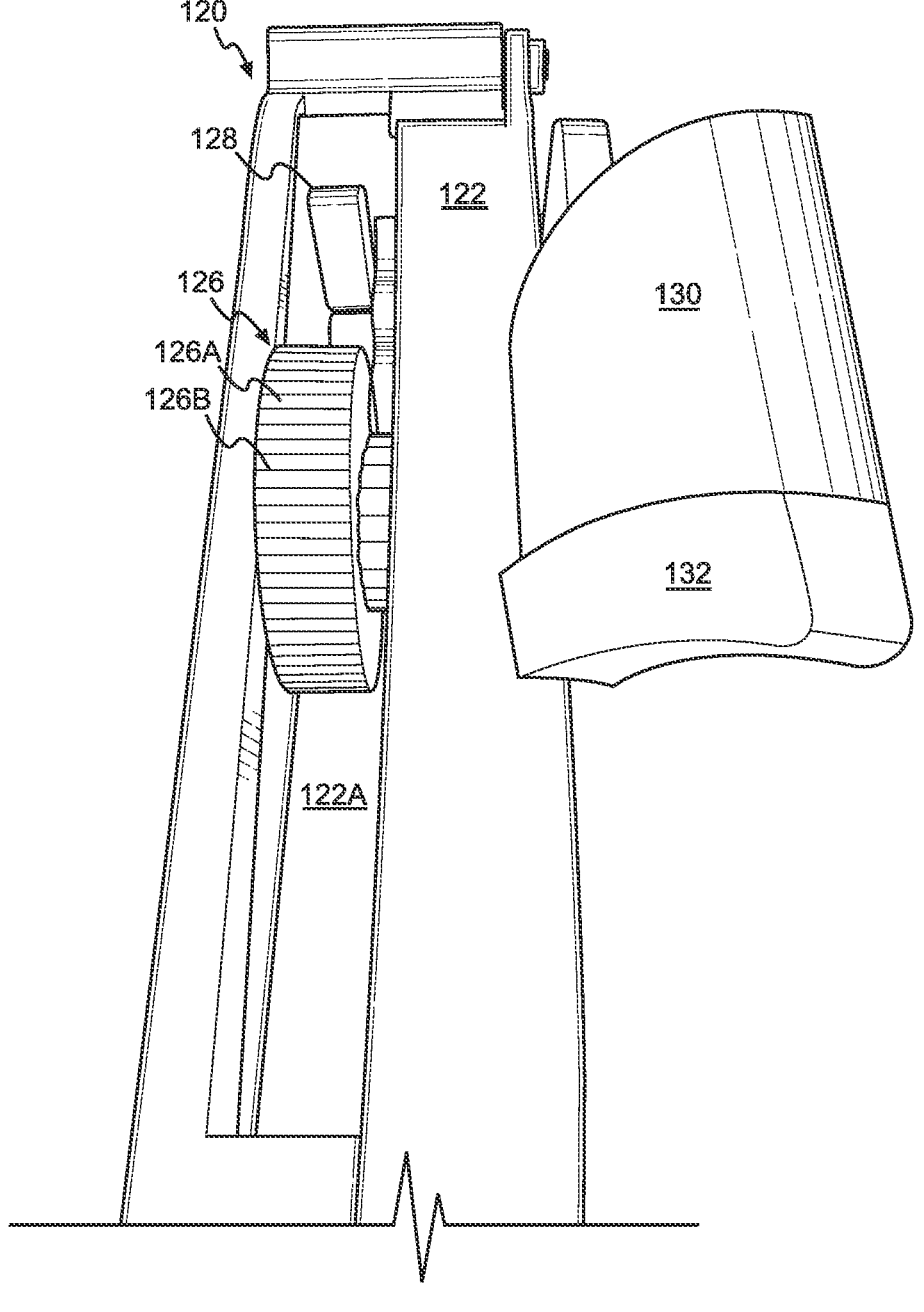
FIG. 2 shows a side prospective view of a jaw thrust appliance, in accordance with one embodiment of the present invention.

FIG. 2 shows a side prospective view of a jaw thrust appliance 100, in accordance with one embodiment of the present invention.

The adjustable slidable bottom 120 may have an elongated horizontal casing 122, a plurality of raised rounded protrusions (FIG. 1, 124), a contact wheel 126, and a lever 128. The adjustable slidable bottom 120 may be movably attached to the bottom portion of the inverted U-shaped base 110. The adjustable slidable bottom 120 may be made of durable material selected from the group consisting of plastic, metal, ceramic, or any combination of each.

The elongated horizontal casing 122 has an elongated interior 122A. The raised rounded protrusions 124 may facilitate contact with the elongated horizontal casing 122 to move the elongated horizontal casing 122 horizontally along the bottom of the inverted U-shaped base 110. The contact wheel 126 may include a plurality of ridges 126A that are disposed on an outer circumference surface 126B of the contact wheel 126. The lever 128 may be depressed to release the contact wheel 126 and allow the elongated horizontal casing 122 to be moved. The contact wheel 126 and the lever 128 may be housed within the elongated interior 122A of the elongated horizontal casing 122.

The ergonomic thumb piece 130 may be disposed directly underneath the adjustable slidable bottom 120. The ergonomic thumb piece 130 may accommodate a user's thumb to move the elongated horizontal casing 122 horizontally along the bottom of the inverted U-shaped base 110. The ergonomic thumb piece 130 may have a covering 132 made of foam rubber or the like to provide comfort to a user while the jaw thrust appliance 100 is being moved. The covering 132 may cushion a user's thumb but also is breathable for additional comfort.

Figure 3:
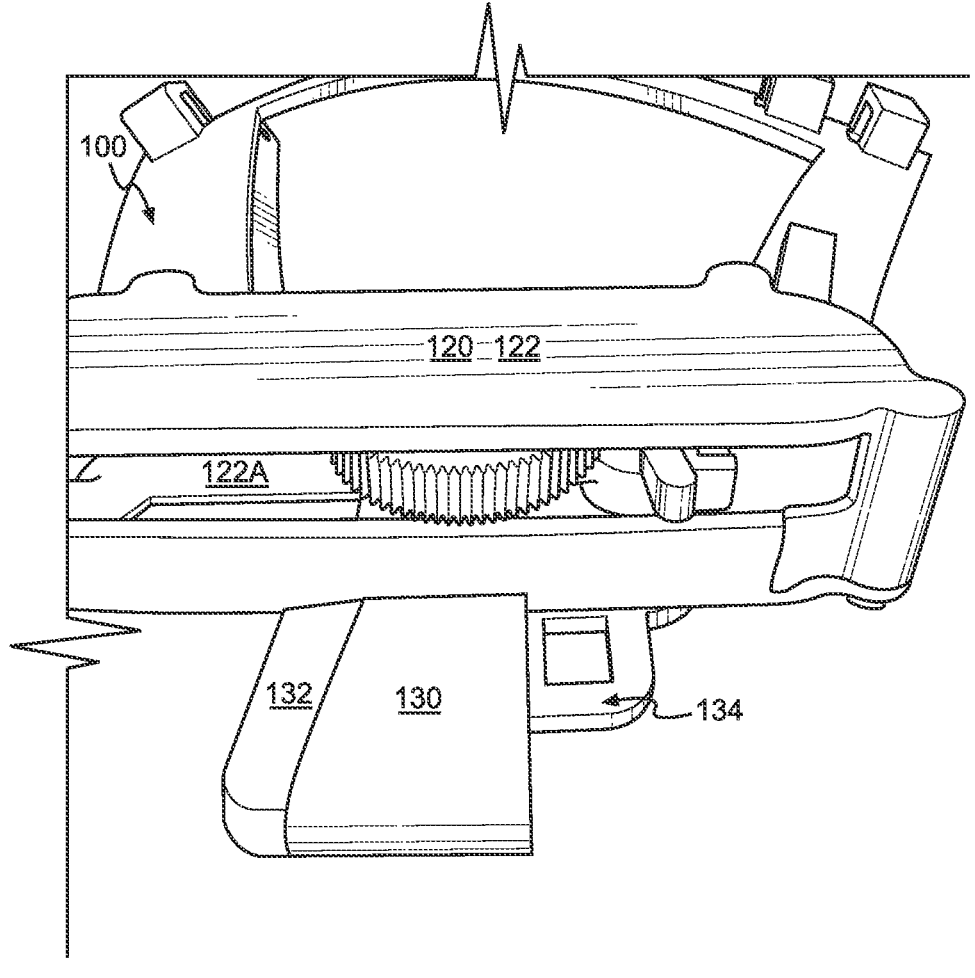
FIG. 3 shows a bottom perspective view of a jaw thrust appliance, in accordance with one embodiment of the present invention.

FIG. 3 shows a bottom perspective view of a jaw thrust appliance 100, in accordance with one embodiment of the present invention.

The adjustable slidable bottom 120 and the ergonomic thumb piece 130 may be attached together and move as a single unit when pushed horizontally. More specifically, the ergonomic thumb piece 130 may be held in a cradle 134 attached to the adjustable slidable bottom 120 within the elongated interior 122A of the elongated horizontal casing 122.

Figure 4:
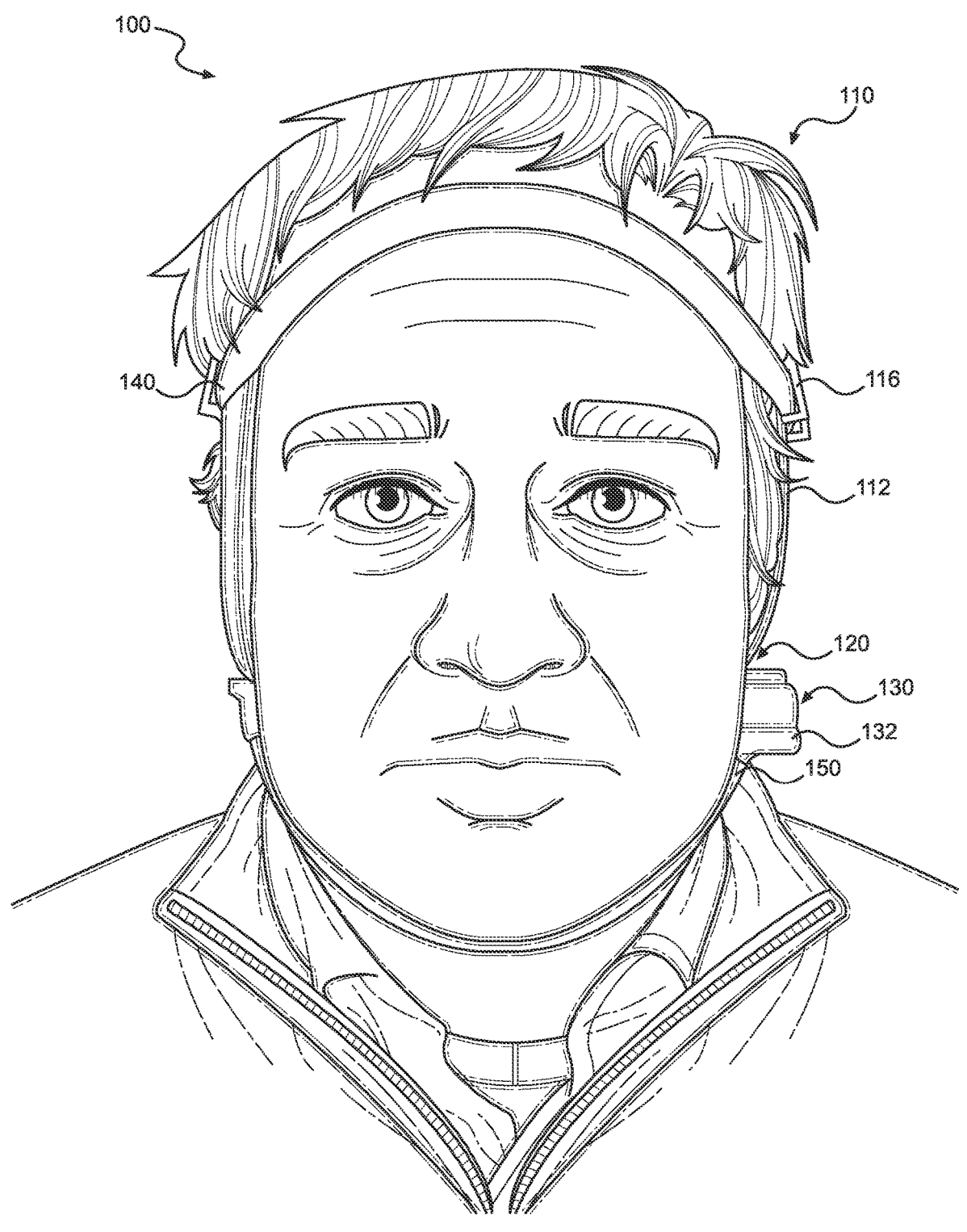
FIG. 4 shows an environmental front perspective view of a jaw thrust appliance, in accordance with one embodiment of the present invention.

FIG. 4 shows an environmental front perspective view of a jaw thrust appliance 100, in accordance with one embodiment of the present invention.

The jaw thrust appliance 100 may include an inverted U-shaped base 110, an adjustable slidable bottom 120, an ergonomic thumb piece 130, a belt 140, and an additional belt 150.

The inverted U-shaped base 110 may include a flat elongated front facing 112. The adjustable slidable bottom 120 may include a plurality of raised inverted U-shaped belt loops 116. The ergonomic thumb piece 130 may include a covering 132 made of foam rubber or the like to provide comfort to the user while the jaw thrust appliance 100 is being moved. The belt 140 may be inserted through the raised inverted U-shaped belt loops 116 to secure the jaw thrust appliance 100 to the user's face. The additional belt 150 may further secure the jaw thrust appliance 100 to the user's face.

Figure 5:
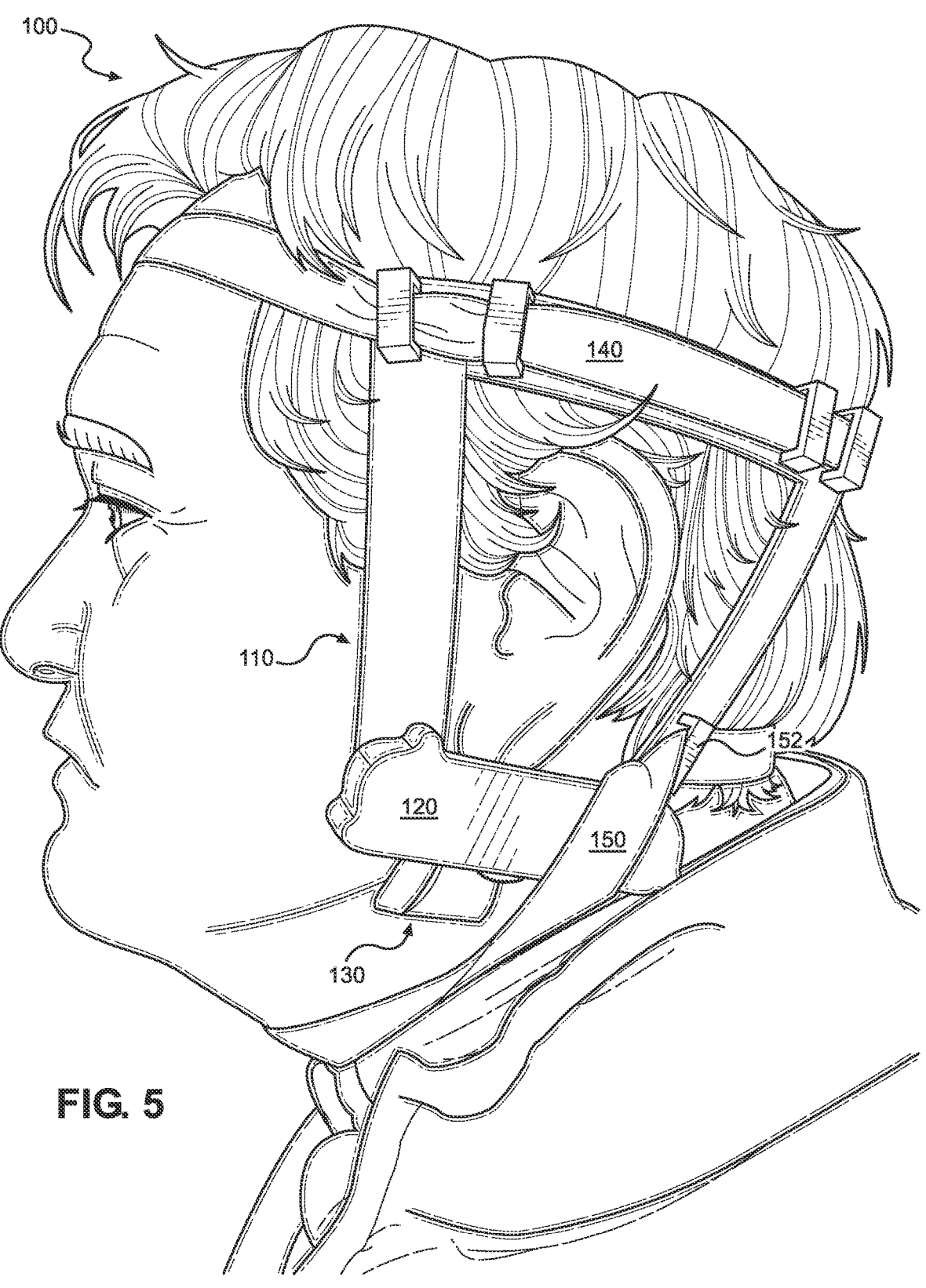
FIG. 5 an environmental side perspective view of a jaw thrust appliance, in accordance with one embodiment of the present invention.

FIG. 5 an environmental side perspective view of a jaw thrust appliance 100, in accordance with one embodiment of the present invention.

The jaw thrust appliance 100 may include an inverted U-shaped base 110, an adjustable slidable bottom 120, an ergonomic thumb piece 130, a belt 140, and an additional belt 150.

The additional belt 150 may also be inserted through a plurality of additional raised inverted U-shaped belt loops 152 to secure the jaw thrust appliance 100 to the user's face.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A jaw thrust appliance, comprising:
an inverted U-shaped base having a bottom portion;
an adjustable slidable bottom movably attached to the bottom portion of the inverted U-shaped base; and
an ergonomic thumb piece disposed directly underneath the adjustable slidable bottom, the adjustable slidable bottom and the ergonomic thumb piece are attached together and move as a single unit when pushed horizontally;
wherein the ergonomic thumb piece accommodates a user's thumb to move an elongated horizontal casing horizontally along the bottom of the inverted U-shaped base.

2. The jaw thrust appliance, according to claim 1, wherein the inverted U-shaped base includes a flat elongated front facing, a padded back facing, a plurality of raised inverted U-shaped belt loops, and an indicia.

3. The jaw thrust appliance, according to claim 2, wherein the flat elongated front facing is adapted to be curved inward to accommodate a user's face.

4. The jaw thrust appliance, according to claim 2, wherein the flat elongated front facing is made of a durable material selected from the group consisting of plastic, metal, ceramic, or any combination of each.

5. The jaw thrust appliance, according to claim 2, wherein the padded back facing is made of foam rubber adapted to provide comfort to a user while the jaw thrust appliance is being worn.

6. The jaw thrust appliance, according to claim 2, wherein the padded back facing is adapted to cushion the user's face but also is breathable for additional comfort.

7. The jaw thrust appliance, according to claim 2, wherein the raised inverted U-shaped belt loops accommodates a belt and an additional belt that are adapted to secure the jaw thrust appliance to the user's face.

8. The jaw thrust appliance, according to claim 7, wherein the raised inverted U-shaped belt loops include a rectangular aperture disposed underneath each of the raised inverted U-shaped belt loops.

9. The jaw thrust appliance, according to claim 2, wherein the indicia is a functional indicia to insure that the user places the inverted U-shaped base properly on the user's face.

10. The jaw thrust appliance, according to claim 2, wherein the indicia is stamped onto the left front portion of the inverted U-shaped base to insure it is not removed or rubbed off.

11. The jaw thrust appliance, according to claim 1, wherein the adjustable slidable bottom includes the elongated horizontal casing, a plurality of raised rounded protrusions, a contact wheel, and a lever.

12. The jaw thrust appliance, according to claim 11, wherein the elongated horizontal casing has an elongated interior.

13. The jaw thrust appliance, according to claim 12, wherein the contact wheel and the lever are housed within the elongated interior of the elongated horizontal casing.

14. The jaw thrust appliance, according to claim 12, wherein the ergonomic thumb piece is held in a cradle attached to the adjustable slidable bottom within the elongated interior of the elongated horizontal casing.

15. The jaw thrust appliance, according to claim 11, wherein the contact wheel includes a plurality of ridges that are disposed on an outer circumference surface of the contact wheel.

16. The jaw thrust appliance, according to claim 11, wherein the lever is depressed to release the contact wheel and allow the elongated horizontal casing to be moved.

17. The jaw thrust appliance, according to claim 11, wherein the adjustable slidable bottom is made of a durable material selected from the group consisting of plastic, metal, ceramic, or any combination of each.

18. The jaw thrust appliance, according to claim 1, wherein the ergonomic thumb piece includes a covering made of foam rubber to provide comfort to a user while the jaw thrust appliance is being moved.

19. The jaw thrust appliance, according to claim 18, wherein the covering is adapted to cushion the user's thumb but also is breathable for additional comfort.

*   *   *   *   *